US007089930B2

(12) United States Patent
Adams et al.

(10) Patent No.: US 7,089,930 B2
(45) Date of Patent: Aug. 15, 2006

(54) WIRELESS HEADS-UP DISPLAY FOR A SELF-CONTAINED BREATHING APPARATUS

(75) Inventors: Jonathan D. Adams, Shaker Heights, OH (US); Joseph Birli, Munson, OH (US); Greg Skillicorn, Glenwillow, OH (US); Gary Claypoole, West Chester, OH (US)

(73) Assignee: Audiopack Technologies, Inc., Garfield Heights, OH (US)

( * ) Notice: Subject to any disclaimer, the term of this patent is extended or adjusted under 35 U.S.C. 154(b) by 75 days.

(21) Appl. No.: 10/224,527

(22) Filed: Aug. 20, 2002

(65) Prior Publication Data

US 2004/0046710 A1 Mar. 11, 2004

(51) Int. Cl.

| | |
|---|---|
| ***B63C 11/02*** | (2006.01) |
| ***A62B 7/02*** | (2006.01) |
| ***A62B 9/00*** | (2006.01) |
| ***A61M 16/00*** | (2006.01) |
| ***A61M 27/00*** | (2006.01) |
| ***G08B 3/00*** | (2006.01) |
| ***G08B 5/00*** | (2006.01) |

(52) U.S. Cl. ........................... 128/201.27; 128/205.23; 128/202.22

(58) Field of Classification Search ........... 128/201.27, 128/205.23, 202.22
See application file for complete search history.

(56) References Cited

U.S. PATENT DOCUMENTS

| | | | |
|---|---|---|---|
| 4,949,072 A * | 8/1990 | Comerford et al. | 340/525 |
| 5,033,818 A * | 7/1991 | Barr | 359/630 |
| 5,097,826 A * | 3/1992 | Gray et al. | 128/204.18 |
| 5,570,688 A * | 11/1996 | Cochran et al. | 128/205.23 |
| 5,860,418 A * | 1/1999 | Lundberg | 128/202.22 |
| 6,032,644 A * | 3/2000 | Bederna et al. | 123/339.15 |
| 6,095,142 A * | 8/2000 | Giorgini | 128/205.23 |
| 6,310,552 B1 * | 10/2001 | Stumberg et al. | 340/573.1 |
| 6,334,440 B1 * | 1/2002 | Cochran | 128/201.27 |

FOREIGN PATENT DOCUMENTS

| | | |
|---|---|---|
| GB | 2283333 A * | 5/1995 |
| WO | WO 02/02191 A1 | 7/2001 |

* cited by examiner

*Primary Examiner*—Henry Bennett
*Assistant Examiner*—Andrea M. Ragonese
(74) *Attorney, Agent, or Firm*—Calfee, Halter & Griswold LLP

(57) ABSTRACT

A system and method of providing a wireless heads-up display for displaying the amount of breathing gas remaining in an associated breathing gas supply is provided. The system has a transmitter and a receiver. The transmitter has a pressure sensor and a controller for interpreting the sensed pressure into levels indicative of the amount of breathing gas remaining in the breathing gas supply. These levels are transmitted via radio frequency to the receiver. The receiver, which can be mounted in a breathing mask, includes a display for displaying the amount of breathing gas remaining in the associated breathing gas supply.

16 Claims, 8 Drawing Sheets

WIRELESS HEADS-UP DISPLAY FOR A SELF-CONTAINED BREATHING APPARATUS

FIELD OF THE INVENTION

The invention relates generally to a Self-Contained Breathing Apparatus (hereinafter SCBA), and more particularly, to a heads-up display for monitoring various parameters of interest to the wearer including, for example, the level of breathing gas in the SCBA.

BACKGROUND OF THE INVENTION

SCBAs are typically used to provide a safe breathing gas supply to a wearer thereof. As such, SCBAs typically include a breathing mask in fluid communication with a breathing gas supply such as, for example, a breathing gas tank. Configured as such, SCBAs are commonly employed by, for example, firefighters and others, when fighting fires or working within environments that contain hazardous gases, microbes or other airborne contaminants. As such, it is vital that the amount of breathing gas remaining in the breathing gas supply be known while the SCBA is in use. One method of presenting this information to the SCBA wearer has been through a mechanical gauge that typically hangs down from the left or right shoulder of the SCBA wearer. However, this arrangement is disadvantageous because the gauge, positioned as such, is outside of the SCBA wearer's field of vision and must be picked up to be read. Firefighters and other users of SCBAs in the heat of action sometimes forget to check their gauges, which can result in hazardous and potentially deadly situations.

In this regard, U.S. Pat. No. 5,097,826 provides a pressure monitoring device for a SCBA that includes visual indicators disposed in the SCBA wearer's field of view to monitor when predetermined pressure levels are reached in the breathing gas supply. The connection between the pressure sensing device and the visual indicators in this and other pressure monitoring devices is typically accomplished through a cable or chord. However, cables and chords are notorious safety and reliability risks in firefighting and other situations where SCBAs are worn. Firefighters often crawl through narrow spaces and cables or chords can get snagged, broken or torn. Hence, a pressure monitoring device for SCBAs that does not suffer from the aforementioned drawbacks is highly desirable.

SUMMARY OF THE INVENTION

According to one embodiment of the present invention, a breathing gas monitor for a breathing apparatus is provided that includes a transmitter and receiver or a transceiver. The transmitter has a pressure sensor configured to sense the pressure level of breathing gas associated with a breathing gas supply and a controller in circuit communication with the pressure sensor and configured to transmit either intermittently or continuously a breathing gas level via a radio frequency signal to the receiver. The receiver has a radio frequency circuit or controller configured to receive the radio frequency signals generated by the transmitter and a display in circuit communication therewith that is configured to indicate the breathing gas level associated with the breathing gas supply to the wearer of the breathing apparatus.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

DETAILED DESCRIPTION OF ILLUSTRATED EMBODIMENT

Prior to discussing the various embodiments of the present invention, a review of the definitions of some exemplary terms used throughout the disclosure is appropriate. Both singular and plural forms of all terms fall within each meaning:

"Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Signal," includes one or more electrical, optical, or electromagnetic signals, analog or digital signals, one or more computer instructions, a bit or bit stream, or the like.

"Software," as used herein, includes but is not limited to one or more computer readable and/or executable instructions that cause a computer or other electronic device to perform functions, actions, and/or behave in a desire manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

"Controller," as used herein, includes but is not limited to any circuit or device that coordinates and controls the operation of one or more input and/or output devices. For example, a controller can include a device having one or more microprocessors or central processing units capable of being programmed to perform input and/or output functions.

Figures 1, 2:
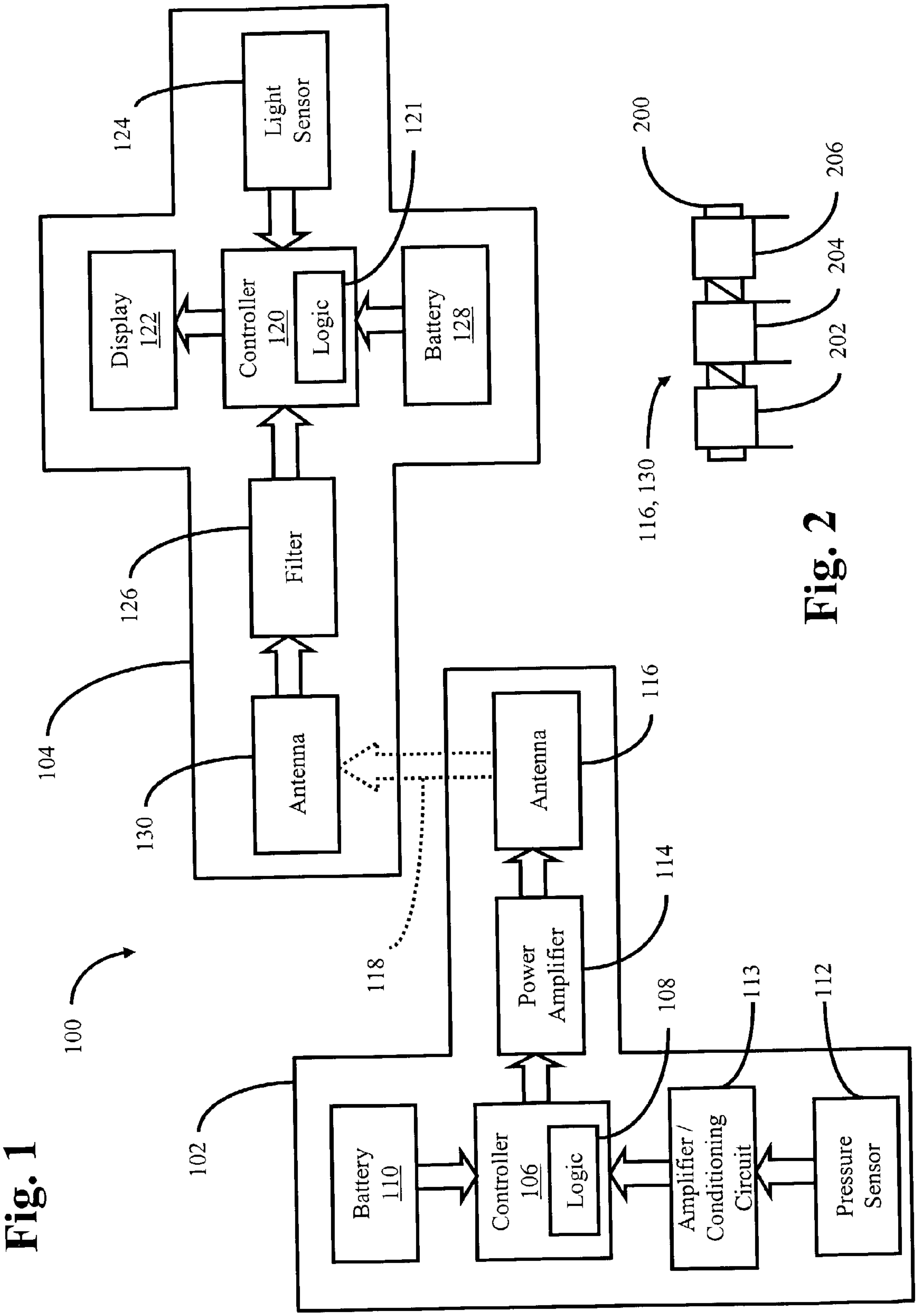
FIG. 1 is a functional block diagram of one embodiment of a system of the present invention.
FIG. 2 is a drawing illustrating one embodiment of an antenna of the present invention.

Illustrated in FIG. 1 is a block diagram of a system 100 of one embodiment of the present invention. System 100 has a transmitter 102 and a receiver 104. The transmitter 102 is preferably configured as a pressure transmitter and has a controller 106, transmitter logic 108, battery 110, pressure sensor 112, power amplifier 114, and antenna 116. In one embodiment, controller 106 is a microprocessor-based controller having a memory, watchdog timer, and one or more input/output ports including an analog-to-digital converter. Transmitter logic 108 preferably resides within the memory of controller 106 and is configured to interpret an analog pressure signal produced by pressure sensor 112 and to generate a breathing gas level signal that is to be transmitted to receiver 104. Alternatively, transmitter logic 108 can reside in an external memory readable by controller 106. An instrumentation amplifier or other signal conditioning circuitry 113 can be incorporated between the sensor 112 and controller 106. In this embodiment, the breathing gas level signal is indicative of the amount of breathing gas remaining in a breathing gas supply, such as a breathing gas tank of a SCBA. Once the breathing gas level signal is determined, controller 106 and logic 108 modulate this information onto a radio frequency carrier through any one of a plurality of suitable modulation techniques creating a communication channel having a baud rate of, for example, 1800 baud. Suitable modulation techniques include Frequency Shift Keying (FSK) and On-Off keying modulation.

In this regard, FSK modulation uses at least 2 distinct frequencies to transmit a digital signal. One frequency represents a digital “1” bit and a second frequency represents a digital “0” bit. Receiver 104 detects these changes in frequency and reconstructs the digital word. One example of using two distinct frequencies includes using a frequency in the range of 30–70 kHz that is frequency shifted by +/−1800 Hz to generate the “1” and “0” bits. On-Off keying modulation employs one signal to transmit the digital “1” bit and the absence of a signal to transmit the digital “0” bit. A transmission according to one embodiment of the present invention includes a transmission having an initialization that includes a long series of “1” bits to signal the start of the transmission. One representative transmission signal of the present invention is discussed in more detail in connection with FIG. 4.

Once modulated, the breathing gas level signal is output to amplifier 114, which drives antenna 116 to generate a radio frequency transmission signal 118. Antenna 116 is preferably a loop stick antenna, which will be discussed in more detail in connection with FIG. 2. Antenna 116 radiates a radio frequency transmission signal 118 into space such that it can be received by receiver 104.

Receiver 104 preferably has a controller 120, receiver logic 121, display 122, light sensor 124, filter 126, battery 128, and antenna 130. Receiver 104 receives the transmission signal 118 from the pressure transmitter 102 through antenna 130 and filter 126. Filter 126 removes unwanted RF signals that are picked up by antenna 130. Antenna 130 is an identical antenna to antenna 116 and can be a loop stick antenna. The transmission signal 118 is demodulated by controller 120 and interpreted by logic 121 to generate a display signal that is sent to display 122. Light sensor 124 reads the amount of ambient lighting available and generates a light level signal that is read by controller 120 and interpreted by logic 121. Logic 121 interprets this light level signal to control the intensity or luminosity of display 122. Configured as such, controller 120 and receiver logic 121 generate a breathing gas level display signal that is indicative of the amount of breathing gas remaining in the breathing supply.

Hence, pressure transmitter 102 through its pressure sensor 112 transmits a radio frequency breathing gas level signal that is received by receiver 104. Receiver 104 demodulates this signal through controller 120 and logic 121 to generate a breathing gas level display signal that is sent to display 122 for display to the wearer of the SCBA.

Shown in FIG. 2 is one embodiment of a loop stick antenna 116, 130 of the present invention. More specifically, the loop stick antenna has a four loops of wires wound around a ferrite core 200. Windings 202, 204, and 206 are wound directly on the ferrite core 200. Winding 204 includes first and second windings wherein the first winding is wound directly on the ferrite core and the second discrete winding is wound over the first winding. In one embodiment, the antenna has an inductance of 103 mH and a resistance of 576+/−10% Ohms. The loop stick antenna provides a wireless link that has a characteristic of an inductive loop system. In particular, the effective transmission range between the pressure transmitter 102 and receiver 104 falls off faster than for non-loop stick antennas. This characteristic reduces cross-coupling between multiple users of the present invention.

Figure 3A:
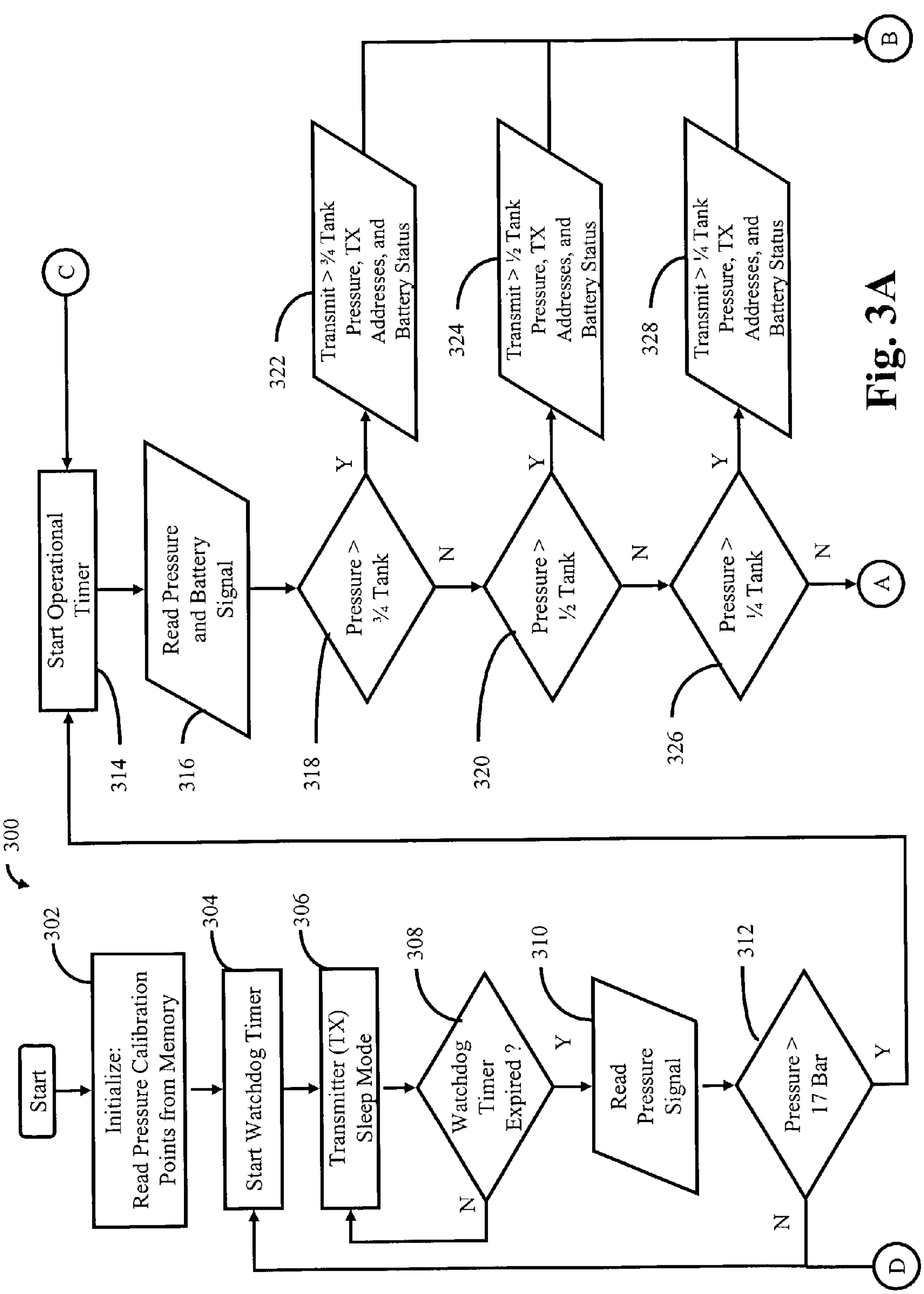
FIGS. 3A and 3B are a flowchart illustrating one embodiment of the transmitter logic of the present invention.
Figure 3B:
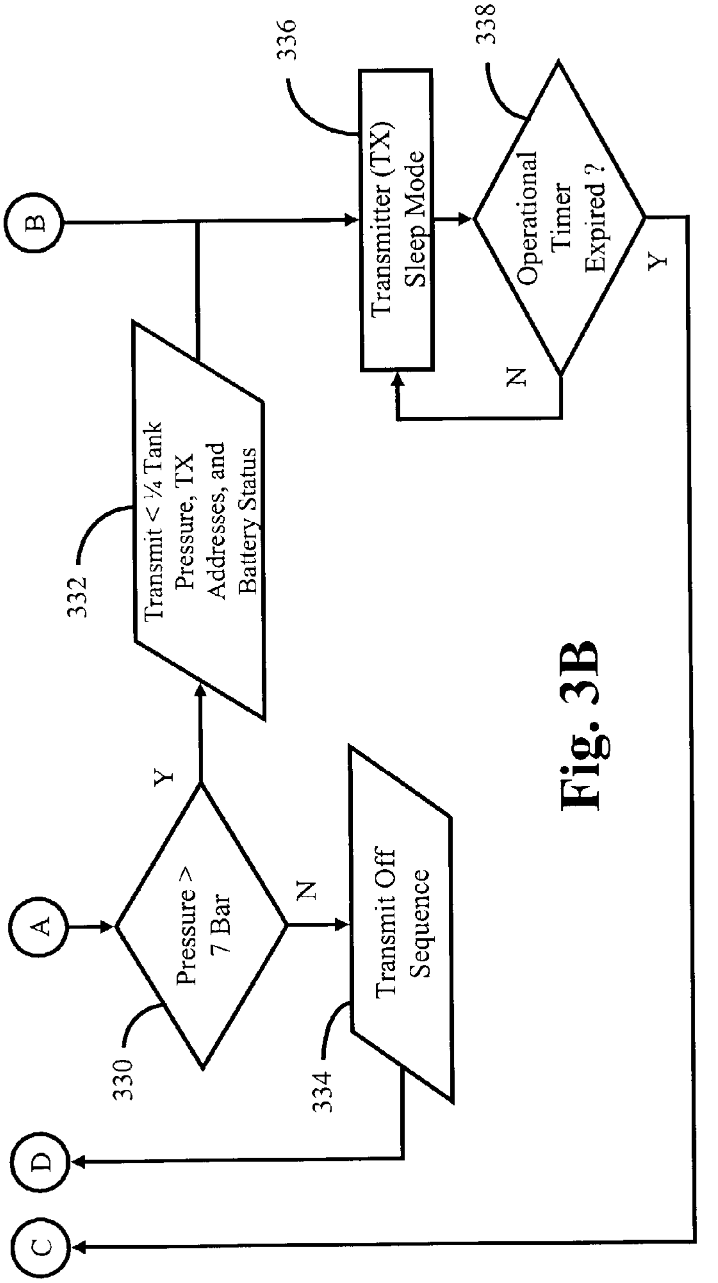

Referring now to FIGS. 3A and 3B, one embodiment 300 of the transmitter logic 108 will now be discussed. As illustrated, the blocks represent functions, actions and/or events performed therein. It will be appreciated that electronic and software applications involve dynamic and flexible processes such that the illustrated blocks can be performed in other sequences different than the one shown. It will also be appreciated by one of ordinary skill in the art that elements embodied as software may be implemented using various programming approaches such as machine language, procedural, object oriented or artificial intelligence techniques. The rectangular elements denote “processing blocks” and represent computer software instructions or groups of instructions. The diamond shaped elements denote “decision blocks” and represent computer software instructions or groups of instructions that affect the execution of the computer software instructions represented by the processing blocks. The remaining parallelogram shaped elements denoted “input or output blocks” and represent computer software instructions or groups of instructions that either read data from various sources or send data to various sources. Alternatively, the processing, decision, and input and output blocks represent steps performed by functionally equivalent circuits such as a digital signal processor circuit or an application specific integrated circuit (ASIC). The flowchart does not depict syntax of any particular programming language. Rather, the flowchart illustrates the functional information one skilled in the art may use to fabricate circuits and/or to generate computer software to perform the processing of the system. It should be noted that many routine program elements, such as initialization of loops and variables and the use of temporary variables are not shown.

In this regard, the logic starts in step 302 where the initialization takes place. In this step, the logic reads the one or more calibration set points from memory. These calibration set points generally calibrate breathing gas pressures with breathing gas levels remaining in a breathing gas supply. After step 302, the logic proceeds to step 304 where a watchdog timer is initiated. In the one embodiment, the timer is set for approximately 10 seconds. Once the watchdog timer has been set, the logic proceeds to step 306 where it directs controller 106 to enter into a sleep mode. This sleep mode is a low energy consumption mode into which controller 106 can enter to conserve energy and prolong battery life. In step 308, the logic tests to determine if the watchdog timer has expired. If the watchdog timer has expired, the logic proceeds to step 310. If the watchdog timer has not expired, the loops back to step 306 and maintains the sleep mode.

In step 310, controller 106 reads the pressure signal generated by pressure sensor 112. In step 312, the logic tests to determine if the pressure signal indicates a pressure greater than a preset minimum such as, for example, 17 Bar. A pressure greater than 17 Bar indicates that the breathing gas supply has been opened and the SCBA is ready for use. If the read pressure is not greater than 17 Bar, then the logic loops back to step 304 and the watchdog timer is once gain initiated for sleep mode. If the read pressure is greater than 17 Bar, then the logic proceeds to step 314.

In step 314, the logic starts an operational timer that is set to a predetermined time period of, for example, ten (10) seconds. Other time periods can also be chosen. After step 314, the logic proceeds to step 316 where the logic reads the pressure signal generated by pressure sensor 112 and the battery 110 voltage level. In steps 318, 320, and 326, the logic determines whether the amount of breathing gas remaining the breathing gas supply is ¾, ½, or ¼ of the total amount capable of being stored in the breathing gas supply. This is done by comparing the read pressure signal to the ¾, ½ and ¼ calibration set points from memory. If the pressure is greater than the ¾ tank set point, then the logic transmits in step 322 a signal indicative of there being more than ¾ of a tank of breathing gas and the battery status (e.g., Hi or Low, Normal or Low, etc). If the pressure level is less than ¾ but greater than ½ of a tank, then the logic transmits in step 324 a signal indicative of there being less than ¾ but more than ½ of a tank of breathing gas and the battery status. If the pressure level is less than ½ but greater than ¼ of a tank, then the logic transmits in step 328 a signal indicative of there being less than ½ but more than ¼ of a tank of breathing gas and the battery status. If, in step 330, the pressure is less than the ¼ tank calibration point but greater than a preset minimum of for example, 7 Bar, then the logic transmits a signal indicative of there being less than ¼ of a tank of breathing gas available and the battery status. If there is less than a preset minimum of breathing gas pressure such as, for example, 7 Bar, then the logic advances to step 334 where an Off sequence is transmitted to receiver 104 indicating that either the breathing gas supply is empty or its output valve has been closed thus stopping the supply of breathing gas. After step 334, the logic loops back to step 304 where the watchdog timer is once again initiated.

After any of transmission steps 322, 324, 328, or 322, the logic advances to step 336 where a sleep mode is once again initiated to conserve energy and prolong battery life. Sleep mode is maintained until the expiration of the operational timer. In step 338, the logic tests to determine whether the operation timer has expired or not. If no, the logic maintains the sleep mode to conserve energy. If yes, the logic loops back to step 314 where the operational timer is once gain initiated and the pressure level read and transmitted.

Hence, one embodiment of the transmitter logic 108 of the present invention provides for periodic transmissions signals associated with the amount of breathing gas remaining in a breathing gas supply. In between these transmissions, the transmitter 102 enters a low-power consumption mode to conserve energy and prolong battery life. Each time the pressure transmitter 102 awakens from it low-power, sleep mode, it reads and transmits a breathing gas level and battery status signal to the receiver 104. After transmission, the transmitter once again enters the sleep mode until it is time to once again awaken for a new transmission.

Figure 4:
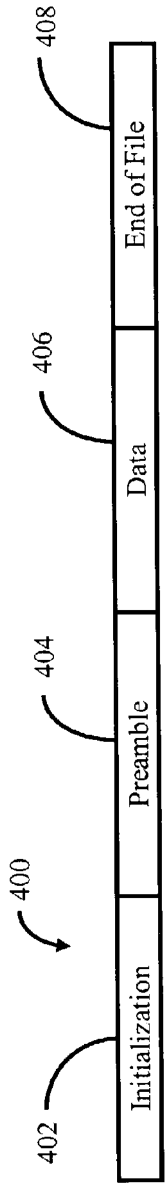
FIG. 4 is a diagram illustrating one embodiment of a transmission signal.

Illustrated in FIG. 4 is one embodiment of information 400 which is transmitted by pressure transmitter 102 to receiver 104. In this regard, the information 400 includes initialization information 402, preamble information 404, data information 406, and end-of-file (EOF) information 408. As described earlier, initialization information 402 can be a long series of digital "1" bits to signal to the start of a transmission. Preamble information 404 can be information that indicates what type of data follows in the data information 406. For example, preamble information 404 can be a first sequence of one of more digital words indicating that the information following in the data information 406 is breathing gas information. Additionally, preamble information 404 can be a second digital word indicating that the information following in the data information 406 is battery status information. Other preamble information 404 can include digital words representing the placing of a new battery in the pressure transmitter, a pressure transmitter off sequence, address/serial number of the transmitter, etc. Data information 406 is preferably at least one digital word corresponding to the type of data referenced in the preamble information 404. The EOF information 408 is preferably a digital word or words that indicates the end of the transmission. Hence, in one embodiment, the initialization information 402 can be 12 "0" bits, the preamble information 404 can be 16 bits (e.g., two 8 bit words) of alternating "1" and "0" bits, the data information 406 can be eight bits (e.g., one 8 bit word), and the EOF information 408 can be eight bits (e.g., one 8 bit word). It should be noted that these bit lengths and word definitions can be varied from that described above without departing from the scope and spirit of the present invention.

Figure 5A:
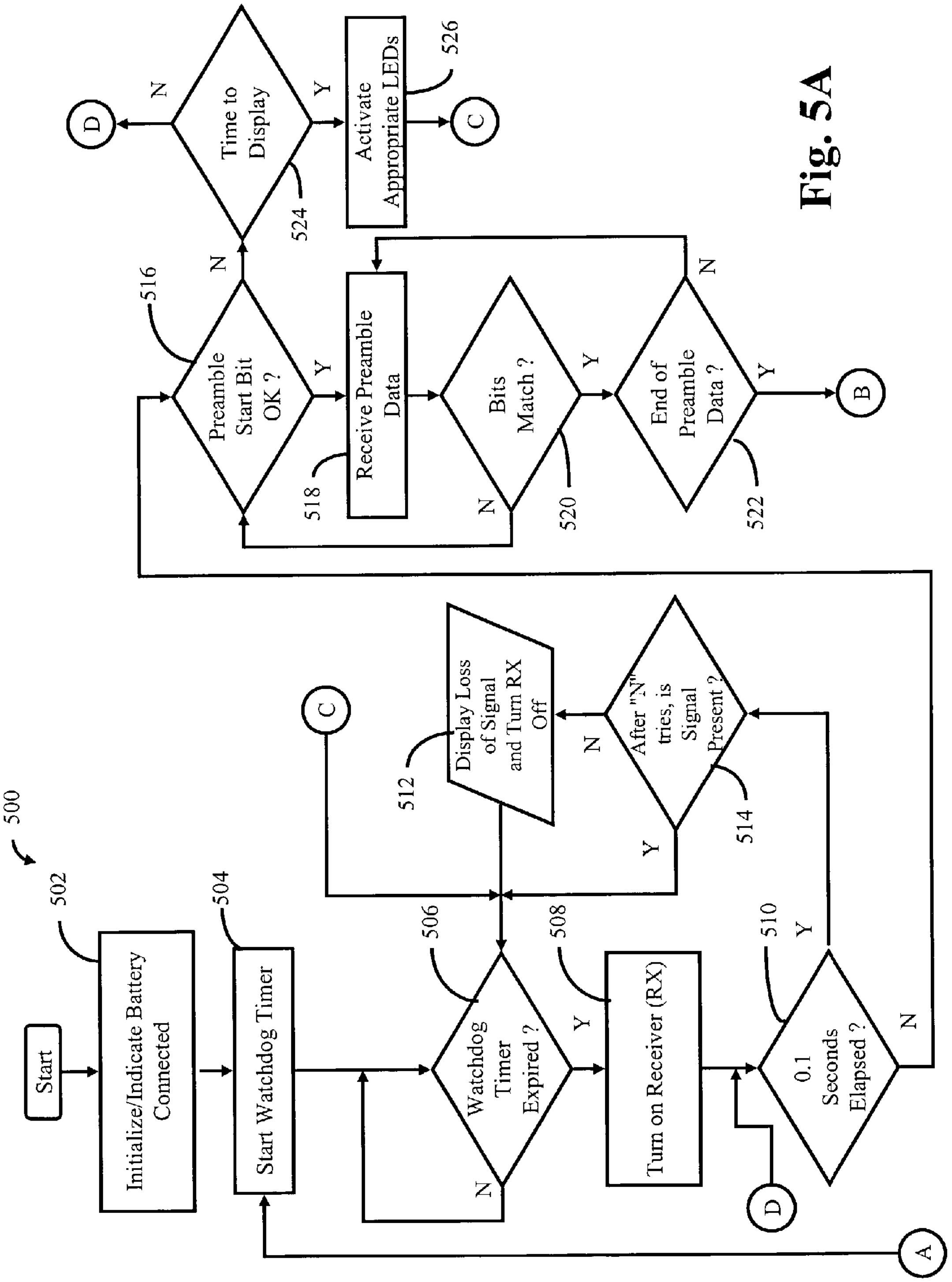
FIGS. 5A and 5B are a flowchart illustrating one embodiment of the receiver logic of the present invention.
Figure 5B:
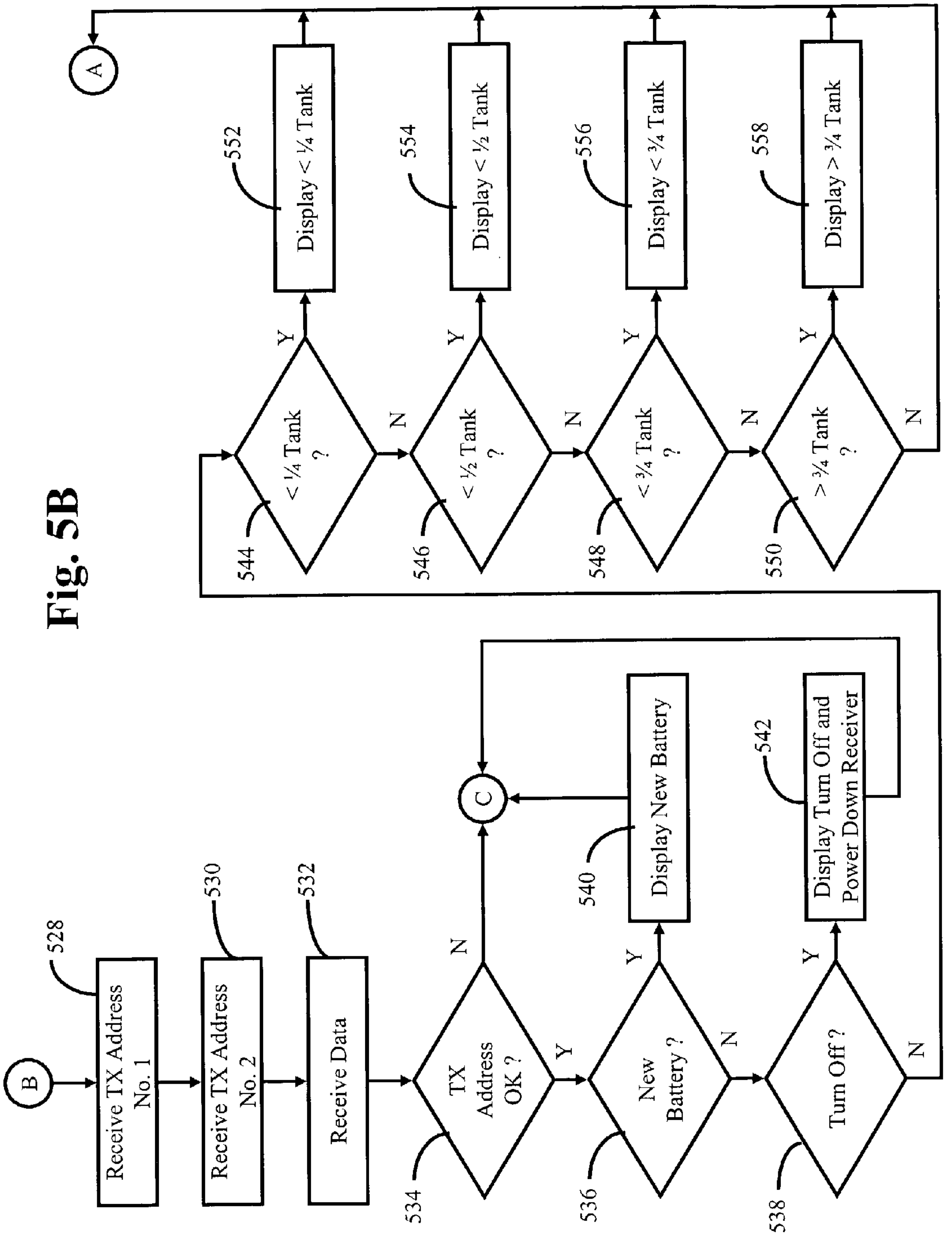

FIGS. 5A and 5B are flowcharts illustrating one embodiment 500 of the receiver logic 121 of the present invention. In this regard, the receiver logic starts in step 502 where upon power-up system initialization occurs including indicating to the user whether a new battery has been connected. In one embodiment, this indication is accomplished by blinking the display LEDs, for example, five times. In step 504, a timer is initiated to time out every 12 seconds. Other time durations are also possible. If in step 506 timer has expired, the logic proceeds to step 508 where the receiver is turned on to listen for and receive radio-frequency transmissions. In step 510, the logic determines if 0.1 second sample time period has expired. Other time periods can also be chosen. This step defines a sample period over which the logic checks to see if preamble data has been received by the receiver.

If a block of data has been received within the 0.1 second sample period, the logic advances to step 516 where it tests to determine if the first bit read is a bit of a preamble portion of a transmission. If yes, steps 518 and 520 check each bit sequentially to determine if a valid preamble has been received. If any bit does not match the expected preamble data, the logic loops back to step 516 and looks for the start of another preamble set of data. If all of the preamble bits match the expected preamble bit data, then the logic advances through step 522 to step 528. If in step 516 the start bit tested is not a preamble start bit, then the logic advances to step 524. In step 524, the logic tests to determine whether it is time to illuminate the pressure display LEDs. The LEDs are preferably illuminated for about 10 seconds of every one minute interval. A timer controls this function. Other illumination schemes are also possible. If it is time to illuminate the LEDs, then the logic advances to step 526 and illuminates the appropriate LEDs in the pressure display according to the desired pressure display illumination scheme. After step 526, the logic loops back to step 506. If it is not time to illuminate the LEDs in the pressure display, the logic loops back to step 510.

Once the preamble data has been confirmed as valid, the logic reads the remaining data received in the transmission in steps 528, 530, and 532. This data includes first and second transmitter addresses or serial numbers and command data from the transmitter. Step 534 tests to determine whether the transmitter addresses or serial numbers received match those defined for the particular receiver. This defining is preferably accomplished by the receiver assuming that the first time it receives a transmitter's addresses and serial numbers, that that is the transmitter that is going to be communicating transmissions to the receiver. All other transmitter transmissions are rejected until the present receiver loses reception in steps 514 and 512.

Steps 536, 538, 544, 546, 548, and 550 test to determine what type of command data has been received from the transmitter. Step 536 tests to determine if new battery command data has been received. If so, step 540 causes the pressure display LEDs to flash a first predetermined pattern for brief time period indicative of a new battery signal. Step 538 tests to determine if turn off command data has been received. If so, step 542 causes the pressure display LEDs to flash a second predetermined pattern for brief period of time indicative of a turn off signal and powers down the receiver to a sleep mode. After either of steps 540 or 542, the logic loops back to step 506.

Step 544 tests to determine if a less than quarter (¼) tank of air command data has been received. If so, the pressure display LEDs are caused in step 552 to display the less than quarter (¼) tank display. Step 546 tests to determine if a less than one-half (½) tank of air command data has been received. If so, the pressure display LEDs are caused in step 554 to display the less than one-half (½) tank display. Step 548 tests to determine if a less than three-quarters (¾) tank of air command data has been received. If so, the pressure display LEDs are caused in step 556 to display the less than three-quarters (¾) tank display. Step 550 tests to determine if a greater than three-quarters (¾) tank of air command data has been received. If so, the pressure display LEDs are caused in step 558 to display the greater than three-quarters (¾) tank display. After any of steps 552, 554, 556, or 558, the logic loops back to step 504.

Figure 6B:
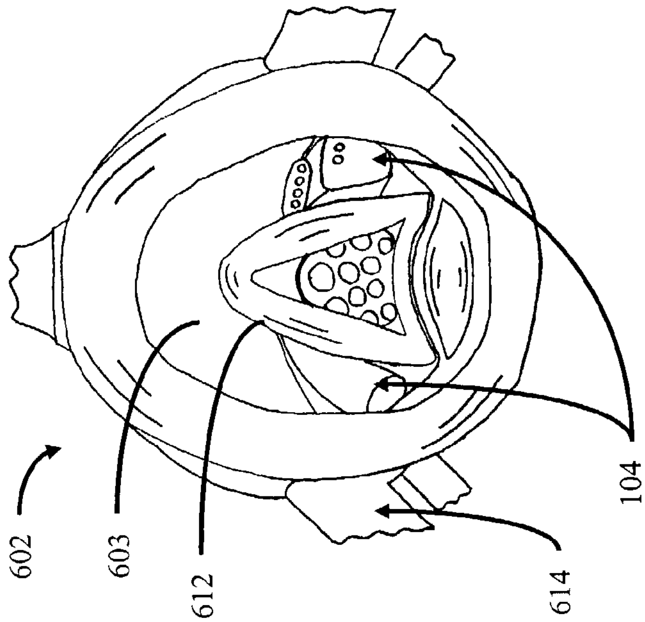
FIGS. 6A and 6B illustrate one embodiment of SCBA system of the present invention.
Figure 6A:
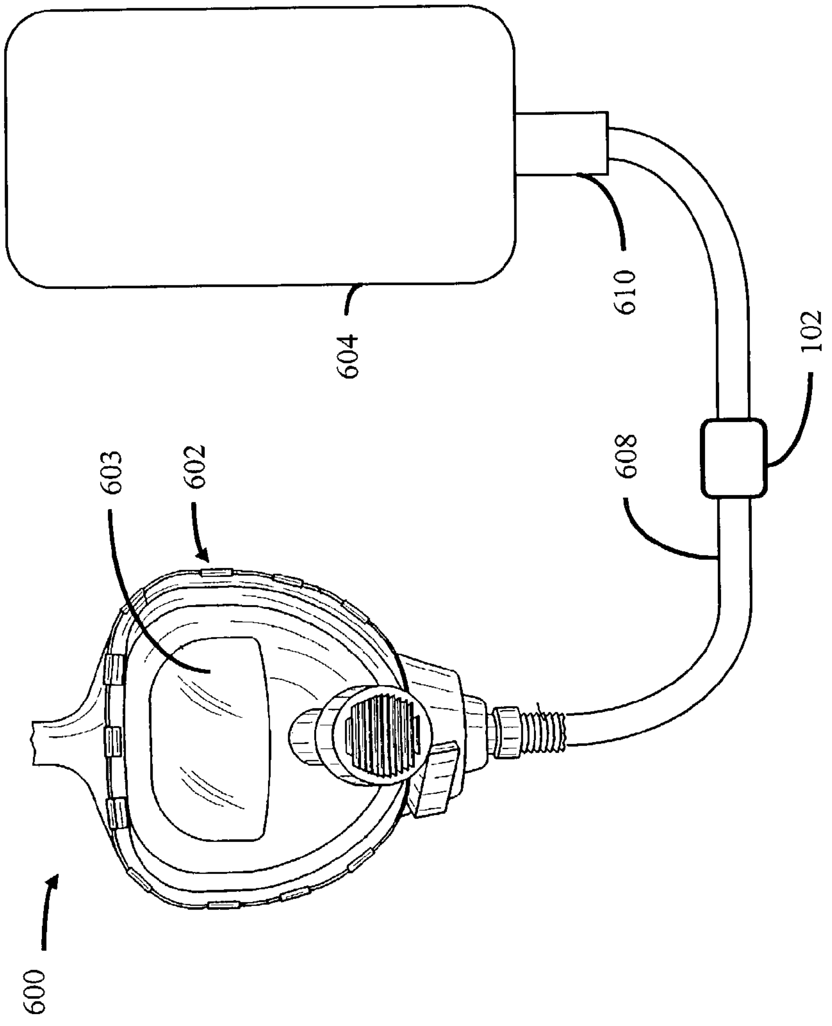

Referring now to FIGS. 6A and 6B, one embodiment 600 of a SCBA system of the present invention is illustrated. The embodiment has a breathing mask 602 that includes a protective shield 603 for allowing the wearer thereof to have a clear field of vision. Mask 602 is in fluid communication with a breathing gas supply 604 via a breathing hose 608 and valve 610. As described above, breathing gas supply 604 can be a SCBA breathing gas tank. In one embodiment, pressure transmitter 102 is disposed in the breathing hose 608, as shown. In other embodiments, pressure transmitter can be located proximate to or integral with valve 610.

As shown in FIG. 6B, mask 602 of the present invention has an oral-nasal breathing port 612 and one or more straps 614 for attaching the mask to the head of a wearer. Additionally, receiver 104 is located within mask 602. In this regard, receiver 104 is preferably located within mask 602 so as to not interfere with the mask's breathing function through port 612 or its field of view characteristic through shield 603. Additionally, receiver 104 is preferably located so as to be in the field of view of a wearer of the mask without limiting the wearer's field of view outside through shield 603.

Configured as such, pressure transmitter 102 senses the pressure level in breathing gas supply 604 and transmits a radio frequency signal to the receiver 104 in mask 602 that is indicative of the amount of breathing gas in the breathing gas supply 604. The receiver 102 being located in the mask 602 wearer's field of view, but not limiting the wearer's field of view outside the mask 602, includes a display indicating the amount of breathing gas remaining in the breathing gas supply 604 and the battery status of the pressure transmitter.

Figure 7A:
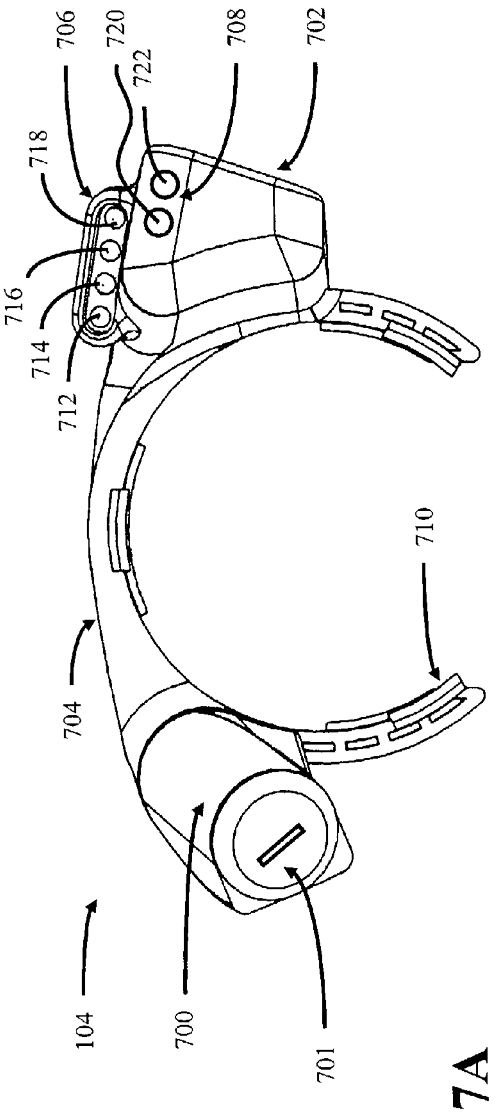
FIGS. 7A and 7B illustrate one embodiment of a heads-up receiver and display of the present invention.
Figure 7B:
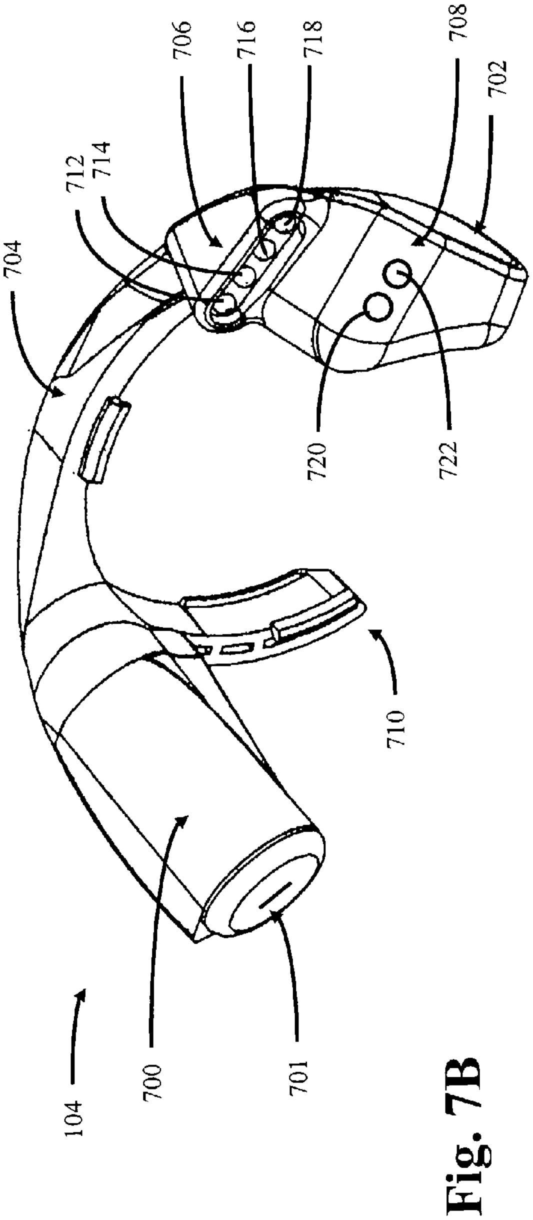

Referring now to FIGS. 7A and 7B, receiver 104 is shown removed from mask 602. In this regard, receiver 104 includes a battery portion 700, display portion 702 and connecting portion 704 therebetween. Battery portion 700 includes a housing within which a battery for powering receiver 104 resides and a removable cover 701 used of accessing the battery and sealing the housing closed. Display portion 702 includes the previously discussed display 122 of FIG. 1 and can include a pressure display 706 and a battery status display 708, each of which can include LEDs or other types of displays. Display portion 702 is also configured to, in some embodiments, house controller 120, logic 121, light sensor 124, filter 126 and antenna 130.

In FIGS. 7A and 7B, pressure display 706 is illustrated as having four (4) LEDs 712, 714, 716, and 718 that represent various levels of breathing gas in the breathing gas supply. More specifically, pressure information is conveyed by display 706 using a combination of LED color and position. The LEDs can be arranged in any orientation including horizontal (as shown), vertical, or any oblique angle and can include a variety of shapes or sizes depending on the space constraints. Additionally, discrete LEDs or a bank or array of LEDs can be employed. Other display 706 configurations include backlit Liquid Crystal Displays (LCDs) or incandescent lamps.

In one embodiment, LEDs 718 and 716 can be green in color when illuminated, while LED 714 can be yellow and LED 712 can be red. When the amount of breathing gas in the tank is greater than ¾ full, all four LEDs (718, 716, 714, and 712) are illuminated. When the amount of breathing gas in the tank is less than ¾ and greater than ½ full, three LEDs (716, 714, and 712) are illuminated. When the amount of breathing gas in the tank is less than ½ and greater than ¼, two LEDs (714 and 712) are illuminated. When the amount of breathing gas in the tank is less than ¼, one LED (712) is illuminated.

Configured as such, LED 718 is illuminated green when the pressure transmitter 102 indicates that the amount of breathing gas remaining the breathing gas supply is greater than ¾ of a tank. LED 716 is illuminated green when the pressure transmitter 102 indicates that the amount of breathing gas remaining the breathing gas supply is less than ¾ but greater than ½ of a tank. LED 714 is illuminated yellow when the pressure transmitter 102 indicates that the amount of breathing gas remaining the breathing gas supply is less than ½ but greater than ¼ of a tank. LED 712 is illuminated red when the pressure transmitter 102 indicates that the amount of breathing gas remaining the breathing gas supply is less than ½ but greater than ¼ of a tank.

Battery status 708 preferably includes receiver battery status LED 720 and transmitter battery status LED 722. In this regard, the receiver battery status LED 720 is preferably yellow and the transmitter battery status LED 722 green. Each LED is off when the battery status is good. Each LED blinks when its battery status falls below a predetermined minimum voltage.

Receiver 104 is fitted with a mounting bracket 710 that provides for the attachment of receiver 104 within mask 602, as shown in FIG. 6B. More specifically, mounting bracket 710 has an arcuate shape configured to fit around the oral-nasal breathing port 612. Configured as such, battery portion 700 resides to one side of the breathing port 612 and display portion 702 resides on the other side of breathing port 612, thereby making effective use of the interior space of mask 602.

Figure 8C:
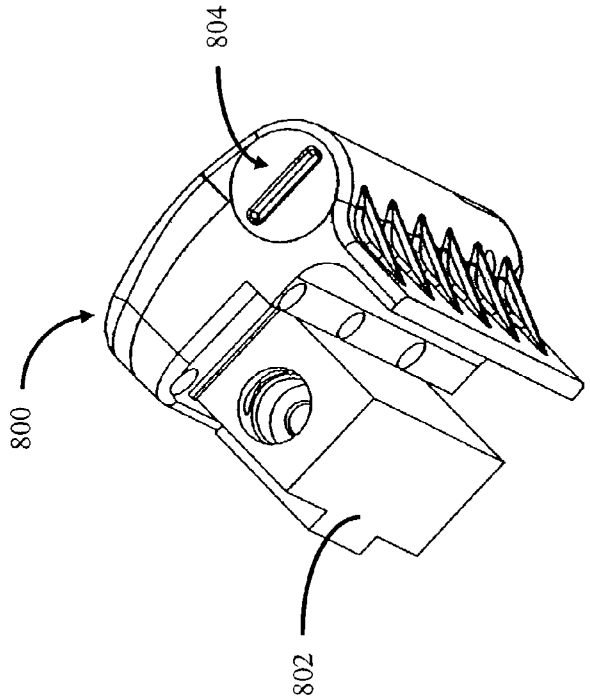
FIGS. 8A, 8B, and 8C illustrate one embodiment of a pressure transmitter of the present invention.
Figure 8A:
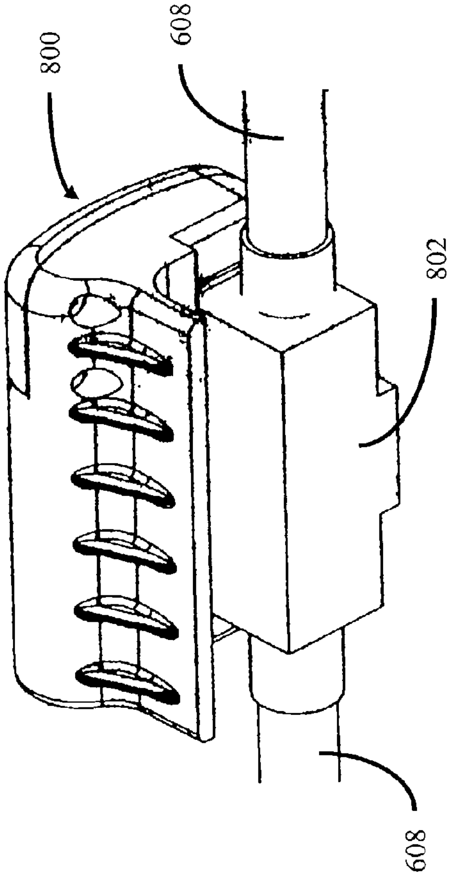
Figure 8B:
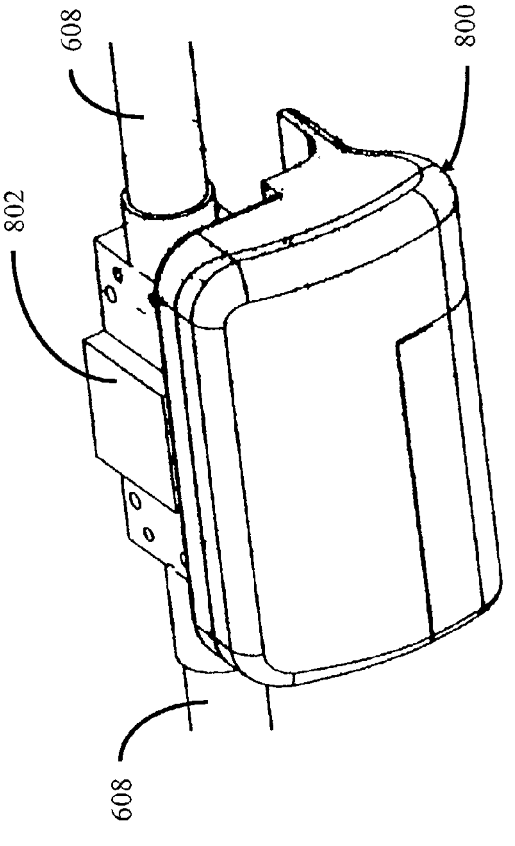

Illustrated in FIGS. 8A, 8B, and 8C is one embodiment 800 of the pressure transmitter 102 of the present invention. More specifically, FIGS. 8A–8C illustrate various views of one embodiment of the pressure transmitter's housing 800 and pressure manifold 802. Housing 800 preferably includes controller 106, logic 108, battery 110, amplifier 114, and antenna 116. Manifold 802 preferably includes pressure sensor 112. Housing 802 also includes a removable battery cover 804 that is removed when changing the transmitter's battery. So configured, housing 800 is affixed to manifold 802. Manifold 802 has first and second orifices whereby the transmitter 102 is inserted inline with breathing gas hoses 608. Configured as such, the pressure of the breathing gas in hose 608 is sensed in manifold 800 by pressure sensor 112. Pressure sensor 112 outputs a pressure level signal to controller 106 in housing 800 for interpretation into a breathing gas level remaining in the breathing gas supply, which is transmitted via radio frequency to the receiver 104 in mask 602. Alternatively, transmitter 800 can be located at the output of valve 610 or integral therewith.

While the present invention has been illustrated by the description of embodiments thereof, and while the embodiments have been described in considerable detail, it is not the intention of the Applicants to restrict or in any way limit the scope of the appended claims to such detail. Additional advantages and modifications will readily appear to those skilled in the art. For example, the data can be from any of several sensors including biometric, temperature, gas detection or others; the display can be any of several visual indicators including but not limited to LEDs, LCDs, incandescent lamps, or others; the information cab also be conveyed as an audible or spoken message through pre-recorded or speech synthesis means. Therefore, the invention, in its broader aspects, is not limited to the specific details, the representative apparatus, and illustrative examples shown and described. Accordingly, departures may be made from such details without departing from the spirit or scope of the applicant's general inventive concept.

What is claimed is:

1. A display system for a breathing apparatus comprising:
- a transmitter comprising:
  - a pressure sensor configured to sense the pressure level of breathing gas associated with a breathing gas supply; and
  - a first controller in circuit communication with the pressure sensor and configured to intermittently transmit a breathing gas level associated with the breathing gas supply via a radio frequency signal;
- a receiver comprising:
  - a second controller configured to receive radio frequency signals generated by the transmitter; and
  - a display in circuit communication with the second controller and configured to indicate the breathing gas level associated with the breathing gas supply;
  - and wherein the receiver is configured to intermittently enter a low power mode upon loss of transmitter signal reception.

2. The display system of claim 1 wherein the first controller is further configured to intermittently read the pressure level from the pressure sensor.

3. The display system of claim 1 wherein the second controller is configured to intermittently process radio frequency signals generated by the transmitter.

4. The display system of claim 1 wherein the transmitter is configured to intermittently enter a low power mode.

5. The display system of claim 1 wherein the transmitter is configured to enter the low power mode after transmitting the breathing gas level.

6. The display system of claim 1 wherein the receiver is configured to intermittently illuminate the display for a predetermined time interval.

7. The display system of claim 1 wherein the receiver is configured to exit the low power mode upon the expiration of a predetermined time interval.

8. The display system of claim 1 wherein the radio frequency signal comprises digital data.

9. The display system of claim 8 wherein the digital data comprises preamble data.

10. The display system of claim 8 wherein the digital data comprises initialization data.

11. The display system of claim 8 wherein the digital data comprises pressure data.

12. The display system of claim 8 wherein the digital data comprises end of signal data.

13. The display system of claim 8 wherein the transmitter comprises an antenna in circuit communication with the first controller.

14. The display system of claim 13 wherein the antenna comprises an inductive loop antenna.

15. A self-contained breathing apparatus comprising:
- a breathing mask;
- a breathing gas supply;
- a transmitter comprising:
  - a pressure sensor configured to sense the pressure level of breathing gas associated with the breathing gas supply; and
  - a first controller in circuit communication with the pressure sensor and configured to intermittently transmit a breathing gas level associated with the breathing gas supply via a radio frequency signal;
- a receiver comprising:
  - a second controller configured to receive radio frequency signals generated by the transmitter; and
  - a display in circuit communication with the second controller and configured to indicate the breathing gas level;
  - and wherein the receiver is configured to intermittently enter a low power mode upon loss of transmitter signal reception.

16. A mask-based system for a self-contained breathing apparatus comprising:
- a mask configured to be in fluid communication with a breathing gas supply:
- a transmitter comprising:
  - a pressure sensor configured to sense the pressure level of breathing gas associated with the breathing gas supply; and
  - a first controller in circuit communication with the pressure sensor and configured to intermittently transmit a breathing gas level associated with the breathing gas supply via a radio frequency signal;
- a receiver comprising:
  - a second controller configured to receive radio frequency signals generated by the transmitter;
  - a display in circuit communication with the second controller and configured to indicate the breathing gas level; and
- the receiver comprising a portion of the mask and wherein the receiver is configured to intermittently enter a low power mode upon loss of transmitter signal reception.

* * * * *